US00PP33810P2

(12) United States Plant Patent
Beekenkamp

(10) Patent No.: US PP33,810 P2
(45) Date of Patent: Jan. 4, 2022

(54) ***CELOSIA* PLANT NAMED 'BKCECAPI'**

(50) Latin Name: *Celosia plumosa*
Varietal Denomination: BKCECAPI

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 17/171,237

(22) Filed: Feb. 9, 2021

(51) Int. Cl.
*A01H 5/02* (2018.01)
*A01H 6/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Celosia* plant named 'BKCECAPI', characterized by its upright plant habit; freely branching habit; freely flowering habit; bright reddish purple-colored flowers arranged on tall and narrow conical compound spikes; and good interiorscape and garden performance.

2 Drawing Sheets

Figure 1:
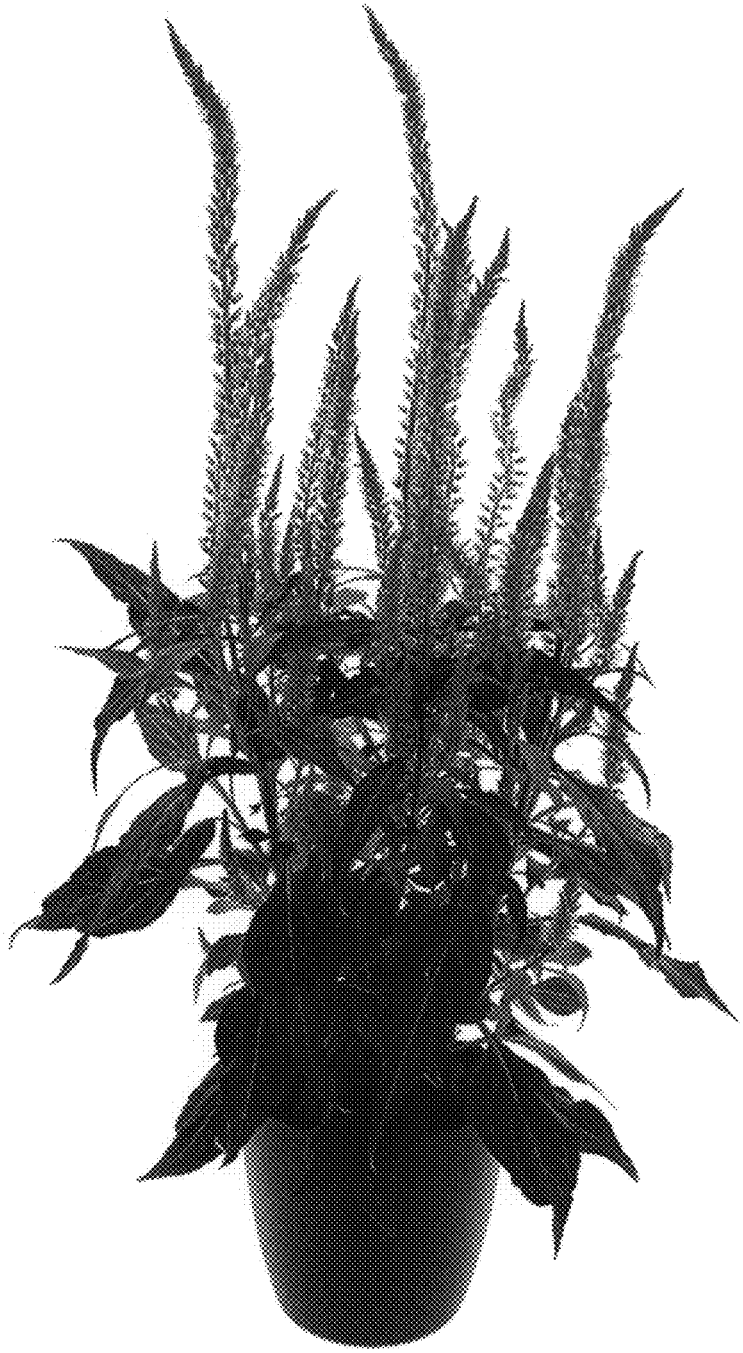

Botanical designation: *Celosia plumosa.*
Cultivar denomination: 'BKCECAPI'.

STATEMENT REGARDING PRIOR DISCLOSURES BY THE INVENTOR/APPLICANT & ASSIGNEE

An European Community Plant Breeder's Rights application for the instant plant was filed by the Assignee, Beekenkamp Plants B.V. of Maasdijk, The Netherlands on Sep. 17, 2020, application number 2020/2210. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Celosia* plant, botanically known as *Celosia plumosa* and hereinafter referred to by the name 'BKCECAPI'.

The new *Celosia* plant is a product of a planned breeding program conducted by the Inventor in Maasdijk, The Netherlands. The objective of the breeding program is to create new *Celosia* plants that have unique and attractive flowers, long flowering period and good interiorscape and garden performance.

The new *Celosia* plant originated from a cross-pollination in June, 2014 in Maasdijk, The Netherlands of a proprietary selection of *Celosia plumosa* identified as code number 99-0245, not patented, as the female, or seed, parent with a proprietary selection of *Celosia plumosa* identified as code number 99-0913, not patented, as the male, or pollen, parent. The new *Celosia* plant was discovered and selected by the Inventor as a single flowering plant from within the progeny of the stated cross-pollination in a controlled environment in Maasdijk, The Netherlands in April, 2015.

Asexual reproduction of the new *Celosia* plant by terminal vegetative cuttings in a controlled environment in Maasdijk, The Netherlands since June, 2015 has shown that the unique features of this new *Celosia* plant are stable and reproduced true to type in successive generations.

SUMMARY OF THE INVENTION

Plants of the new *Celosia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKCECAPI'. These characteristics in combination distinguish 'BKCECAPI' as a new and distinct *Celosia* plant:

1. Upright plant habit.
2. Freely branching habit.
3. Freely flowering habit.
4. Bright reddish purple-colored flowers arranged on tall and narrow conical compound spikes.
5. Good interiorscape and garden performance.

Plants of the new *Celosia* differ from plants of the female parent selection in the following characteristics:

1. Plants of the new *Celosia* are taller than plants of the female parent selection.
2. Leaves of plants of the new *Celosia* are lighter green in color than leaves of plants of the female parent selection.
3. Plants of the new *Celosia* have bright reddish purple-colored flowers whereas plants of the female parent selection have purple-colored flowers.

Plants of the new *Celosia* differ from plants of the male parent selection in the following characteristics:

1. Plants of the new *Celosia* are taller than plants of the male parent selection.
2. Leaves of plants of the new *Celosia* are lighter green in color than leaves of plants of the male parent selection.
3. Plants of the new *Celosia* have bright reddish purple-colored flowers whereas plants of the male parent selection have yellow-colored flowers.

Plants of the new *Celosia* can be compared to plants of *Celosia plumosa* 'BKCELANP', disclosed in U.S. Plant Pat. No. 29,590. In side-by-side comparisons, plants of the new *Celosia* differ primarily from 'BKCELANP' in the following characteristics:

1. Plants of the new *Celosia* are taller than plants of 'BKCELANP'.
2. Leaves of plants of the new *Celosia* are lighter green in color than leaves of plants of 'BKCELANP'.
3. Plants of the new *Celosia* have bright reddish purple-colored flowers whereas plants of 'BKCELANP' have bright pink-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet (FIG. 1) comprises a side perspective view of a typical flowering plant of 'BKCECAPI' grown in a container.

Figure 2:
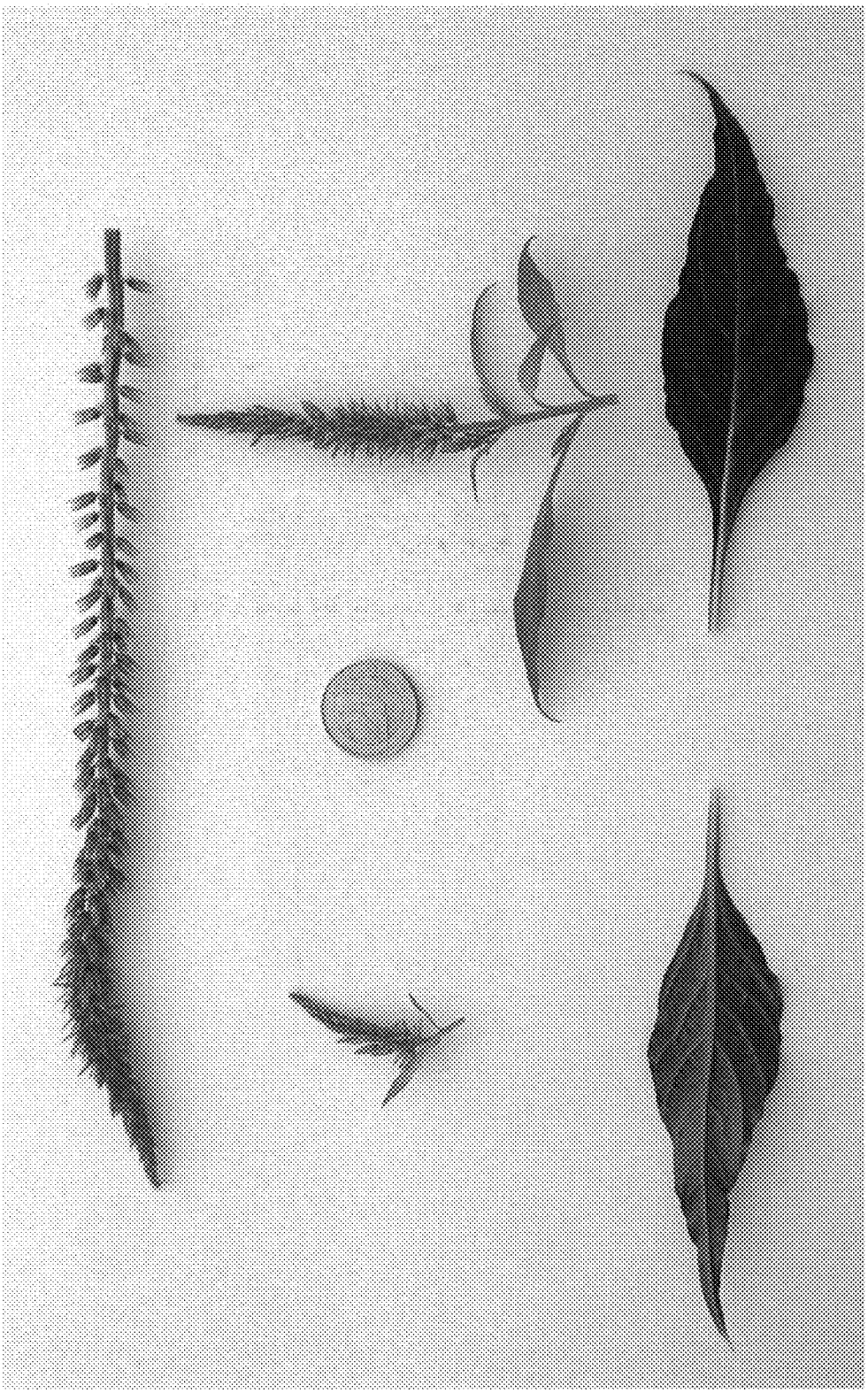

The photograph on the second sheet (FIG. 2) is a close-up view of typical developing and developed inflorescences and the upper and lower surfaces of leaves of 'BKCECAPI'.

DETAILED BOTANICAL DESCRIPTION

The aforementioned photographs and following observations, measurements and values describe plants grown in 11-cm containers during the autumn in a glass-covered greenhouse in Maasdijk, The Netherlands and under commercial cultural practices typical of *Celosia* production. During the production of the plants, day temperatures averaged 20° C. and night temperatures averaged 18° C. Plants were pinched one time and were 15 weeks old when the photographs and description were taken. In the following description, color references are made to The Royal Horticultural Society Colour Chart, 2015 Edition, except where general terms of ordinary dictionary significance are used.

Botanical classification: *Celosia plumosa* 'BKCECAPI'.

Parentage:

*Female, or seed, parent*.—Proprietary selection of *Celosia plumosa* identified as code number 99-0245, not patented.

*Male, or pollen, parent*.—Proprietary selection of *Celosia plumosa* identified as code number 99-0913, not patented.

Propagation:

*Type*.—By terminal vegetative cuttings.

*Time to initiate roots, summer*.—About 16 days at temperatures ranging from about 19° C. to 21° C.

*Time to initiate roots, winter*.—About 19 days at temperatures ranging from about 19° C. to 21° C.

*Time to produce a rooted young plant, summer*.—About 22 days at temperatures ranging from about 19° C. to 21° C.

*Time to produce a rooted young plant, winter*.—About 26 days at temperatures ranging from about 19° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous annual typically grown as a potted plant; upright plant habit; elliptic to obovate in overall shape; freely branching habit with about two basal branches each with about six lateral branches developing per plant; moderately vigorous to vigorous growth habit and moderate growth rate.

*Plant height, soil level to top of foliar plane*.—About 29.7 cm.

*Plant height, soil level to top of floral plane*.—About 53 cm.

*Plant width* (*spread*).—About 33 cm.

*Lateral branches*.—Length: About 12.4 cm. Diameter: About 3 mm. Internode length: About 1 cm. Strength: Moderately strong. Aspect: About 30° from vertical. Texture and luster: Smooth, glabrous; slightly glossy. Color, developing: Close to 150D slightly tinged with close to 68C. Color, developed: Close to N170D; distally, strongly tinged with close to 151A and 151B; towards the base, close to 63B.

Leaf description:

*Arrangement*.—Alternate; simple.

*Length*.—About 10.2 cm.

*Width*.—About 3.3 cm.

*Shape*.—Narrowly ovate to close to lanceolate.

*Apex*.—Long apiculate.

*Base*.—Attenuate.

*Margin*.—Entire, moderately undulate.

*Texture and luster, upper and lower surfaces*.—Slightly rugose, glabrous; slightly glossy.

*Venation pattern*.—Pinnate.

*Color*.—Developing leaves, upper surface: Close to 143B and 144A. Developing leaves, lower surface: Close to 143C. Fully expanded leaves, upper surface: Close to 137B; irregularly flushed with close to 200A; venation, close to 157D tinged with close to 65B. Fully expanded leaves, lower surface: Close to 146B; venation, close to N148C.

*Petioles*.—Length: About 1.7 cm. Diameter: About 2.5 mm to 3 mm. Strength: Low, flexible. Texture and luster, upper and lower surfaces: Smooth, glabrous; moderately glossy. Color, upper surface: Close to 157D; towards the margins, close to 148A to darker than 148A; proximal end, tinged with close to 65A. Color, lower surface: Close to 157A to 157B; towards the margins, close to 146; proximal end, tinged with close to 65B.

Flower description:

*Flower type and arrangement*.—Single rotate flowers arranged in long and narrow conical terminal compound spikes; flowers face upright to outwardly depending on position on spike.

*Flowering habit*.—Freely flowering habit with about 180 flowers per inflorescence and about 2,500 flowers developing per plant during the flowering season.

*Fragrance*.—None detected.

*Natural flowering season*.—Plants begin flowering about eight weeks after pinching; under natural season conditions, flowering continuous from spring into the autumn in The Netherlands.

*Postproduction longevity*.—Inflorescences of the new *Celosia* have good longevity and plants maintain good substance for about six weeks on the plant; flowers persistent.

*Inflorescence height*.—About 27.6 cm.

*Inflorescence diameter*.—About 1.8 cm.

*Flower diameter*.—About 9 mm by 9 mm.

*Flower height*.—About 6 mm.

*Flower buds*.—Length: About 7 mm. Diameter: About 2 mm. Shape: Lanceolate. Texture and luster: Smooth, glabrous; glossy. Color: Close to 64A to 64B.

*Petals*.—None observed.

*Sepals*.—Quantity and arrangement: Typically six per flower arranged in two whorls. Length: About 6.5 mm. Width: About 1.5 mm. Shape: Lanceolate. Apex: Narrowly acute. Base: Obtuse. Margin: Entire. Texture and luster, inner and outer surfaces: Smooth, glabrous; glossy. Color: When opening, upper surface: Close to N74D; midvein, close to 72B. When opening, lower surface: Close to N74C to N74D; midvein, close to 72B. Fully opened, upper surface: Close to N74D to lighter than N74D; midvein, close to 72B; color becoming closer to 76B and midvein, closer to 72C, with development. Fully opened, lower surface: Close to N74D; midvein, close to 72B; color becoming closer to 76B and midvein, closer to 72C, with development.

*Peduncles*.—Length: About 27.3 mm. Diameter: About 3 mm. Angle: Upright to about 25° from vertical. Strength: Moderately strong. Texture and luster: Smooth, glabrous; matte. Color: Close to between 69A and 182D strongly flushed with close to 148B.

*Pedicels*.—Length: About 1 mm. Diameter: About 0.75 mm. Angle: About 50° from peduncle axis. Strength: Moderately strong. Texture and luster: Smooth, glabrous; matte. Color: Close to 70C.

*Reproductive organs*.—Stamens: Quantity per flower: Five. Filament length: About 3 mm. Filament color: Close to N74A to N74B. Anther size: About 0.3 mm by 1 mm. Anther shape: Narrowly oblong. Anther color: Close to 183C. Pollen amount: Scarce. Pollen color: Close to 158D. Pistils: Quantity per flower: One. Length: About 4 mm. Stigma diameter: About 1 mm. Stigma shape: Club-shaped, three-parted. Stigma color: Close to N74A. Style length: About 3.5 mm. Style color: Close to N74B. Ovary color: Close to N74B.

*Seeds and fruits*.—To date, seed and fruit development have not been observed on plants of the new *Celosia*.

Pathogen & pest resistance: To date, plants of the new *Celosia* have not been observed to be resistant to pathogens and pests common to *Celosia* plants.

Garden performance: Plants of the new *Celosia* have been observed to have good garden performance and to be suitable for USDA Hardiness Zones 9 to 12.

It is claimed:

1. A new and distinct *Celosia* plant named 'BKCECAPI' as illustrated and described.

* * * * *